US012569664B2

(12) United States Patent　　　(10) Patent No.:　US 12,569,664 B2
Landy, III et al.　　　　　　　　(45) Date of Patent:　Mar. 10, 2026

(54) FLOW-REVERSING VALVE, AND ASSOCIATED HYPERTHERMIA TREATMENT METHOD AND SYSTEM

(71) Applicant: Belmont Instrument, LLC, Billerica, MA (US)

(72) Inventors: John Joseph Landy, III, Billerica, MA (US); Alexander Rick, Derry, NH (US); Tristan Dion, Hudson, NH (US); Skylar Nesheim, Brighton, MA (US); David Dumais, Billerica, MA (US); Yeu Wen Tseng, Watertown, MA (US); Chuong Vu, Revere, MA (US)

(73) Assignee: Belmont Instrument, LLC, Billerica, MA (US)

( * ) Notice: Subject to any disclaimer, the term of this patent is extended or adjusted under 35 U.S.C. 154(b) by 906 days.

(21) Appl. No.: 17/760,981

(22) PCT Filed: Sep. 1, 2020

(86) PCT No.: PCT/US2020/048903
§ 371 (c)(1),
(2) Date: Mar. 16, 2022

(87) PCT Pub. No.: WO2021/055165
PCT Pub. Date: Mar. 25, 2021

(65) Prior Publication Data
US 2022/0355094 A1　　Nov. 10, 2022

Related U.S. Application Data

(60) Provisional application No. 62/903,450, filed on Sep. 20, 2019.

(51) Int. Cl.
*A61M 39/22*　　(2006.01)
*A61M 1/36*　　(2006.01)
(Continued)

(52) U.S. Cl.
CPC ........ *A61M 39/223* (2013.01); *A61M 1/3621* (2013.01); *A61M 2039/0264* (2013.01); *A61M 2039/1088* (2013.01)

(58) Field of Classification Search
CPC ........ A61M 39/223; A61M 2039/0264; A61M 2039/1088
(Continued)

(56) References Cited

U.S. PATENT DOCUMENTS 5,207,643 A * 5/1993 Davis ................. A61M 39/223
604/80
5,894,011 A * 4/1999 Prosl .................... A61M 39/18
210/636
(Continued)

FOREIGN PATENT DOCUMENTS

WO　WO-2018/183210 A1　10/2018
WO　WO-2021/055165 A1　3/2021

OTHER PUBLICATIONS

Young's Modulus of Elasticity—Values for Common Materials; https://www.engineeringtoolbox.com/young-modulus-d_417.html (Year: 2003).*
(Continued)

*Primary Examiner* — Emily L Schmidt
*Assistant Examiner* — Martin A Radomski
(74) *Attorney, Agent, or Firm* — Choate, Hall & Stewart LLP; William R. Haulbrook; Peter A. Flynn

(57) ABSTRACT

The present disclosure describes a flow reversing valve, along with associated methods and systems for providing forward flow, reverse flow, and bypass flow modes of operation, and integrating them into patient treatment systems, including those used for treating and inducing hyperthermia.

18 Claims, 7 Drawing Sheets

(51) Int. Cl.
   *A61M 39/02*      (2006.01)
   *A61M 39/10*      (2006.01)

(58) Field of Classification Search
   USPC .......................................................... 604/65
   See application file for complete search history.

(56)                    References Cited

U.S. PATENT DOCUMENTS

| | | | | |
|---|---|---|---|---|
| 6,086,762 | A * | 7/2000 | Guala | A61M 1/3641 |
| | | | | 210/232 |
| 6,596,234 | B1 | 7/2003 | Schnell et al. | |
| 2001/0031222 | A1 | 10/2001 | Schnell et al. | |
| 2006/0079827 | A1* | 4/2006 | Jensen | A61M 39/223 |
| | | | | 604/6.1 |
| 2006/0089603 | A1* | 4/2006 | Truitt | A61M 39/02 |
| | | | | 604/246 |
| 2014/0088482 | A1 | 3/2014 | Schlaeper et al. | |

OTHER PUBLICATIONS

International Preliminary Report on Patentability for PCTUS2020048903, 8 pages (mailed Mar. 15, 2022).
International Search Report for PCTUS2020048903, 5 pages (mailed Dec. 9, 2020).
Written Opinion for PCTUS2020048903, 7 pages (mailed Dec. 9, 2020).

* cited by examiner

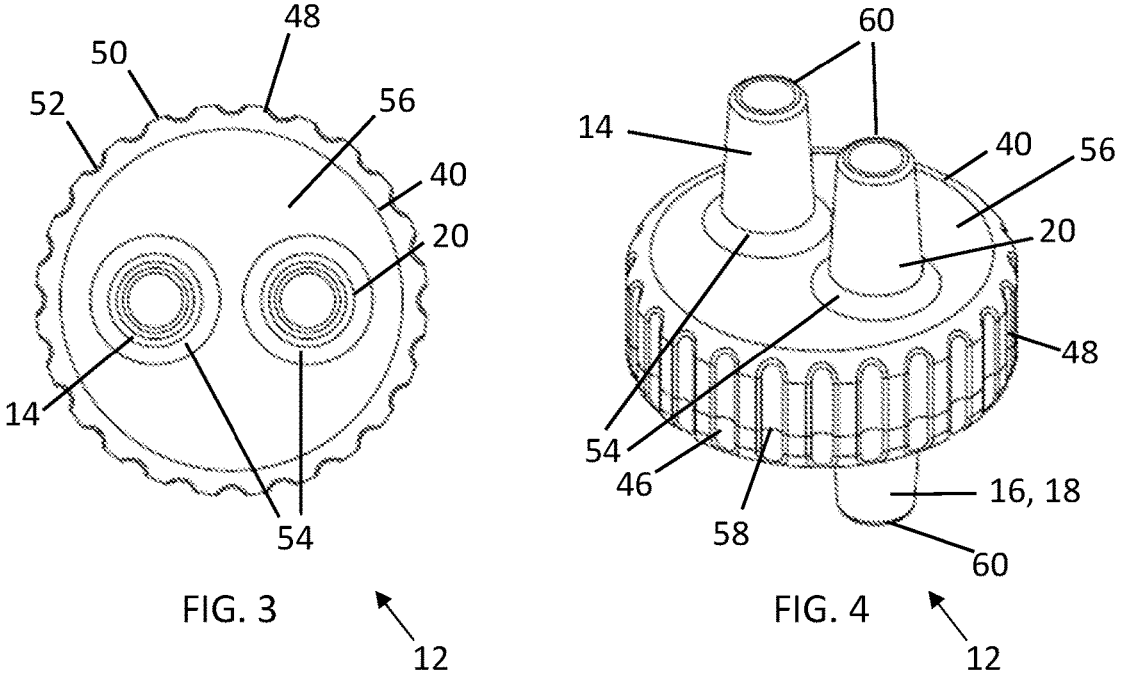
FIG. 3
FIG. 4
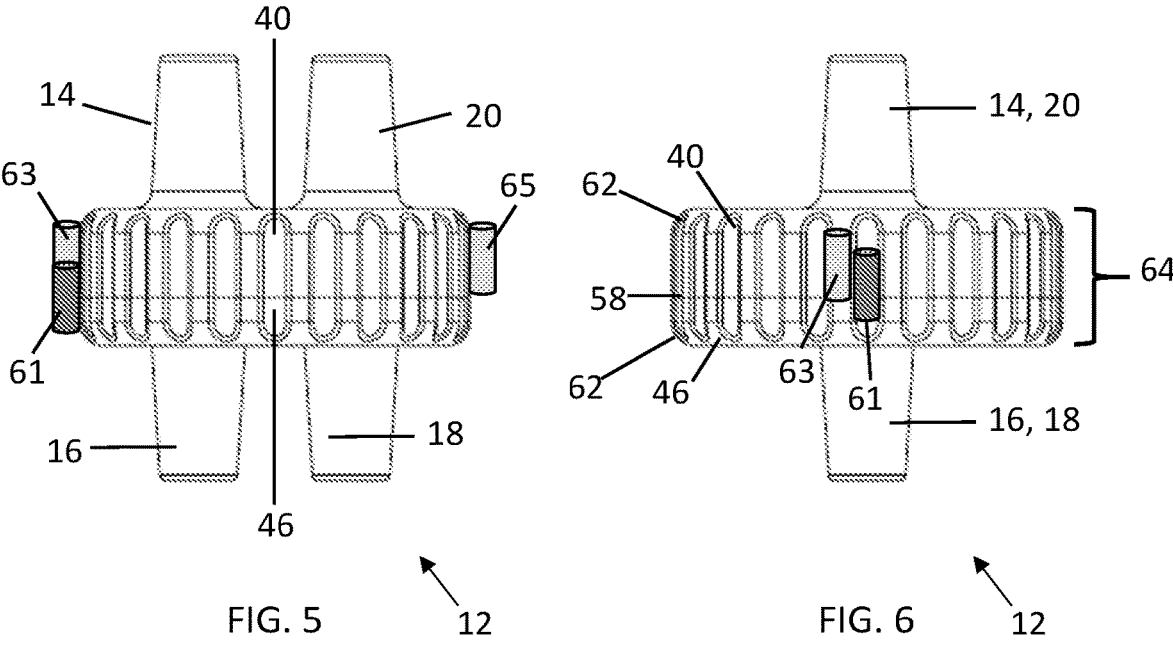
FIG. 5
FIG. 6

1802 — FLUIDLY CONNECT PUMP, HEATER AND RESERVOIR

1804 — FLUIDLY CONNECT SYSTEM LINES TO FRV

1806 — FLUIDLY CONNECT PATIENT LINES TO FRV

1808 — INITIATE A FLOW OF THERAPEUTIC FLUID THROUGH FRV

1810 — CHECK LINE FOR CLOG / BLOCKAGE

1812 — ROTATE FRV 180 DEGREES INITIATING REVERSE FLOW

1814 — RE-CHECK LINE FOR BLOCKAGE

1816 — ROTATE FRV BACK TO START POSITION (0 DEG)

1818 — RESUME PATIENT TREATMENT

1820 — REPEAT 1802-1818 AS NEEDED

1800

FLOW-REVERSING VALVE, AND ASSOCIATED HYPERTHERMIA TREATMENT METHOD AND SYSTEM

RELATED APPLICATIONS

This application claims priority to U.S. Provisional Application No. 62/903,450 filed on Sep. 20, 2019, the entire contents of which are hereby incorporated by reference.

FIELD

The subject matter described herein relates to systems and methods for directing fluid within a patient treatment system.

BACKGROUND

In modern health care systems, fluid heating systems are regularly used for various kinds of medical treatments including treatment of hemorrhaging, treatment of tumors, treatment of circulating tumor cells (CTCs), as well as hyperthermia.

Hyperthermia refers to the increase of an individual's body temperature above his or her normal range. Research has shown that temperatures greater than 41° C. can damage cancer cells, usually without significant damage to normal tissues. While there are multiple methods of inducing hyperthermia by either direct skin contact or radiant heating, many physicians favor an extracorporeal heat exchange circuit (for example, using patient blood, dialysate and/or other fluids) to raise patient body temperatures. An extracorporeal heat exchange circuit, for example, may include lavaging the peritoneal cavity at the debulking site (i.e., the location from which the tumor has been removed). Temperature and time may be interrelated with respect to tumor necrosis and the risk of toxicity to normal cells. The inefficiency of free floating tumor cells to dissipate heat due to their separation from the vascular system subjects the tumor cells to thermal damage, anaerobic metabolism, and local acidosis, making the tumor cells more vulnerable to injury and causing the tumor cells to undergo apoptosis.

In systems used to raise the temperature of lavage fluids, it is not uncommon for fluid lines to become clogged due to blockages and/or debris. This may apply to dialysis systems, blood transfusion equipment, systems for treating or inducing hyperthermia, systems for administering antibiotics and other anti-microbial drugs, as well as other systems. For example, systems for treating and/or inducing hyperthermia are designed to lavage the peritoneal cavity with warmed fluids. During this process, debris can accumulate in various fluid lines (including, but not limited to patient return lines, and/or suction lines). The debris build up may be handled in two primary ways. In an open procedure a return "suction" line is isolated and the debris is manually removed. In a closed procedure (i.e., where the lines are sewn into a patient), the pump is stopped and the inlet and outlet lines are re-plumbed temporarily. In many cases, reducing the flow through the inlet line may also help to reduce a blockage in the patient return line. However, this typically results in reduced therapy to the patient.

In both the open and closed systems, it is not uncommon for patient treatments to be delayed and/or stopped while equipment is taken out of service for cleaning, and to remove clogs, blockages, and/or debris. Not only does this present an inconvenience to the patient, but it also puts the patient at increased risk of infection, while also potentially endangering the well-being of the patient due to delays in the administration of treatment(s). The costs of treatment also rise with increasing treatment times due to both the cost of the treating personnel, as well as the cost of the equipment. Further improvements to existing heating system technologies may result in lower overall patient treatment times, as well as increases in the effectiveness of patient treatments.

SUMMARY OF THE INVENTION

The present disclosure provides methods and systems for providing forward flow, reverse flow, and bypass flow modes of operation, and integrating them into patient treatment systems, including those used for treating and inducing hyperthermia. Using a reverse flow mode of operation, clogs, debris, and other blockages that may accumulate in one or more patient and/or system lines may be cleared from the system. A flow reversing valve (FRV) according to the present disclosed embodiments enables reverse flow operation (as well as forward flow and bypass modes), without requiring any components or tubing to be connected or disconnected from the system. The FRV can be switched from one mode of operation to another in less than a second, without having to stop the flow of fluid through the system (i.e., a fluid pump can continually run while the position of the FRV is being switched). The FRV also enables reverse flow in one or more portions of the system while allowing other portions of the system to maintain fluid flow in the forward direction.

In one aspect, the invention is directed to a flow reversing valve including: a top portion; a retaining ring coupled to the top portion; a bottom portion at least partially disposed between the top portion and the retaining ring; and a gasket radially disposed around the bottom portion and at least partially disposed between the top portion and the bottom portion. A first rotation of the bottom portion relative to the top portion causes flow in at least one portion of the flow reversing valve to reverse direction.

In some embodiments, the valve may include: a first leg disposed within the top portion; a second leg disposed within the bottom portion; a third leg disposed within the bottom portion; and a fourth leg disposed within the top portion.

In some embodiments, the first leg is fluidly coupled directly to the second leg before the first rotation, and the third leg is fluidly coupled directly to the fourth leg before the first rotation.

In some embodiments, the first leg is fluidly coupled directly to the third leg after the first rotation, and the second leg is fluidly coupled directly to the fourth leg after the first rotation.

In some embodiments, at least one of the top portion and the retaining ring includes a knurled circumference.

In some embodiments, at least one of the first leg, the second leg, the third leg, and the fourth leg includes at least one taper at a transition with the respective top portion and/or bottom portion.

In some embodiments, the first rotation is from about 120 degrees to about 240 degrees.

In some embodiments, the first rotation is from about 150 degrees to about 210 degrees.

In some embodiments, the first rotation is from about 165 degrees to about 195 degrees.

In some embodiments, a second rotation of from about 80 degrees to about 100 degrees of the bottom portion relative to top portion causes at least one fluid flow to bypass at least one portion of the flow reversing valve.

In some embodiments, a second rotation of from about 85 degrees to about 95 degrees of the bottom portion relative to top portion causes at least one fluid flow to bypass at least one portion of the flow reversing valve.

In some embodiments, at least one of the top portion and the bottom portion includes at least one of a trough and a curved flow passage disposed therein.

In some embodiments, the bottom portion includes: an upper lip; a lower lip disposed beneath the upper lip; and a race disposed between the upper lip and the lower lip. The race may include a smaller diameter than each of the upper lip and the lower lip. The gasket may be disposed around the race between the upper lip and the lower lip.

In some embodiments, the retaining ring is coupled to the top portion via a threaded connection and/or a compression fit.

In some embodiments, the valve may include at least one detent coupled to the top portion or the bottom portion; and at least one stop coupled to the top portion or the bottom portion. The detent may contact the at least one stop at a rotation of zero (0) degrees, ninety (90) degrees, and/or one-hundred and eighty (180) degrees.

In some embodiments, the gasket is composed of a first material, and each of the top portion, the bottom portion and the retaining ring are composed of one or more second materials. The Young's modulus of the first material may be less than the Young's modulus of the one or more second materials.

In some embodiments, the top portion includes a female fitting disposed at the bottom of the top portion; and the bottom portion includes a male fitting disposed at the top of the bottom portion. The male fitting may be inserted into the female fitting, the female fitting may be disposed radially outward of the male fitting, and the female fitting may be disposed radially inward of the retaining ring.

In another aspect, the invention is directed to a system for treating a patient including: at least one pump; a flow reversing valve fluidly connected to the pump; a patient inlet line fluidly connected to the flow reversing valve; a patient return line fluidly connected to the flow reversing valve; a system inlet line fluidly connected to the flow reversing valve; and a system outlet line fluidly connected to the flow reversing valve. A first rotation of at least one portion of the flow reversing valve causes flow in at least one portion of the system to reverse directions.

In some embodiments, the system outlet line is fluidly coupled directly to the patient inlet line before the first rotation, and the patient return line is fluidly coupled directly to the system inlet line before the first rotation.

In some embodiments, the system outlet line is fluidly coupled directly to the patient return line after the first rotation, and the patient inlet line is fluidly coupled directly to the system inlet line after the first rotation.

In some embodiments, the system includes at least one fluid reservoir fluidly connected to the pump, and at least one fluid heater fluidly connected to the pump.

In some embodiments, the pump is downstream of the fluid reservoir, the fluid heater is downstream of the pump, and the flow reversing valve is downstream of the fluid heater.

In some embodiments, at least one of the patient inlet line and the patient return line includes dual lumen lines.

In another aspect, the invention is directed to a method of treating a patient including: providing at least two system fluid lines and at least two patient fluid lines that are each fluidly connected to a flow reversing valve; initiating a flow of fluid through the flow reversing valve; checking at least one of the at least two system fluid lines and the at least two patient fluid lines for at least one of a blockage and debris; and rotating at least one portion of the flow reversing valve through a first angle, thereby resulting in flow reversal in the two system fluid lines and/or the two patient fluid lines.

In some embodiments, the method includes re-checking at least one of the at least two system fluid lines and the at least two patient fluid lines for at least one of a blockage and debris, after rotating at least one portion of the flow reversing valve through the first angle.

In some embodiments, the method includes rotating at least one portion of the flow reversing valve back to an initial position after re-checking the two system fluid lines and the two patient fluid lines.

In some embodiments, the method includes resuming at least one patient treatment.

In some embodiments, the method includes rotating at least one portion of the flow reversing valve through a second angle thereby causing flow to bypass at least one portion of the at least two system fluid lines and the at least two patient fluid lines.

In some embodiments, causing flow to bypass at least one portion of the at least two system fluid lines and the at least two patient fluid lines includes: bypassing a pump system, bypassing a patient system, and/or initiating a double bypass flow mode of operation.

Throughout the description, where systems or compositions are described as having, including, or comprising specific components, or where methods are described as having, including, or comprising specific steps, it is contemplated that, additionally, there are systems or compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the claims presented herein. The Background section is presented for purposes of clarity and is not meant as a description of prior art with respect to any claim.

BRIEF DESCRIPTION OF THE DRAWING

A full and enabling disclosure of the present disclosed embodiments, including the best mode thereof, directed to one of ordinary skill in the art, is set forth in the specification, which makes reference to the appended figures, in which:

FIG. 3 illustrates a top view of a flow reversing valve according to aspects of the present embodiments;

FIG. 4 illustrates a perspective view of a flow reversing valve according to aspects of the present embodiments;

FIG. 5 illustrates a front view of a flow reversing valve according to aspects of the present embodiments;

FIG. 6 illustrates a side view of a flow reversing valve according to aspects of the present embodiments;

DESCRIPTION OF THE INVENTION

Figure 1:
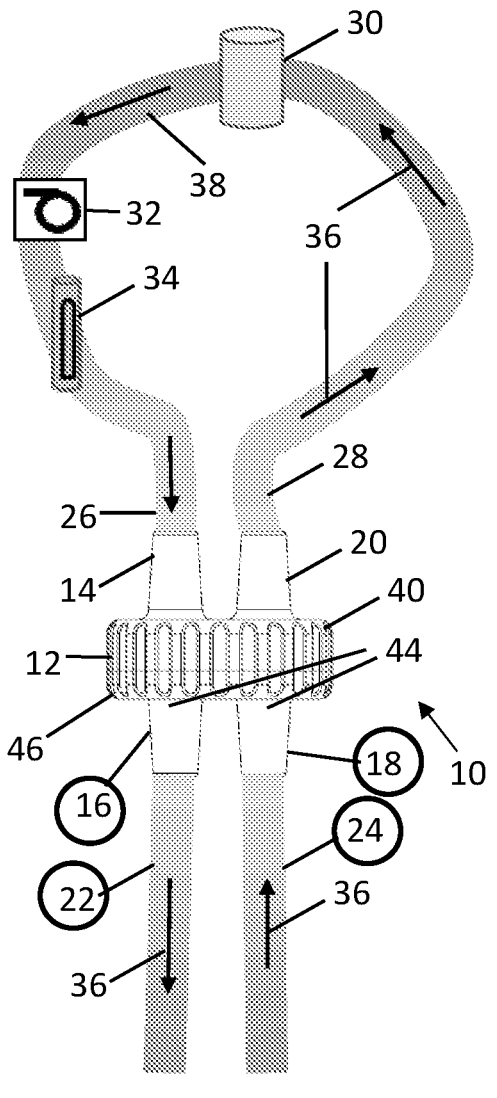
FIG. 1 illustrates a first configuration of a patient treatment system according to aspects of the present embodiments.

Reference will now be made in detail to the present disclosed embodiments, one or more examples of which are illustrated in the accompanying drawings. The detailed description uses numerical and/or letter designations to refer to features in the drawings. Like or similar designations in the drawings and description have been used to refer to like or similar parts of the present embodiments.

The present disclosure provides methods and systems for providing forward flow, reverse flow, and bypass flow modes of operation, and integrating them into patient treatment systems. A flow reversing valve (FRV) according to the present disclosed embodiments enables all three modes of operation, without requiring any components or tubing to be connected or disconnected from a system. The FRV can be switched from one mode of operation to another in less than a second, without having to stop the flow of fluid through the system (i.e., a fluid pump can continually run while the position of the FRV is being switched). The FRV also enables reverse flow in one or more portions of the system while allowing other portions of the system to maintain fluid flow in the forward direction.

These and other features, aspects and advantages of the present invention will become better understood with reference to the following description and appended claims. The accompanying drawings, which are incorporated in and constitute a part of this specification, illustrate embodiments of the present disclosure and, together with the description, serve to explain the principles of the present embodiments.

Patient Treatment Systems

FIG. 1 illustrates a first configuration of a patient treatment system 10 according to aspects of the present embodiments. The system 10 may include a fluid reservoir 30 for storing a therapeutic fluid (such as blood, dialysate, and/or other lavage fluids). The fluid reservoir 30 may be sized such that it has a capacity from about one liters to about ten liters, and/or all sub-ranges in between. In other embodiments, the fluid reservoir 30 may be sized such that it has a capacity from about two liters to about eight liters. In other embodiments, the fluid reservoir 30 may be sized such that it has a capacity from about three liters to about six liters. In other embodiments, the fluid reservoir 30 may be sized such that it has a capacity from about four liters to about five liters. From the fluid reservoir 30, therapeutic fluid may flow via tubing 38 to a pump 32 disposed downstream of the fluid reservoir 30. The tubing 38 may have an outer diameter from about 0.1 inches to about 1.0 inches. In other embodiments, the tubing 38 may have an outer diameter from about 0.15 inches to about 0.5 inches. In other embodiments, the tubing 38 may have an outer diameter from about 0.2 inches to about 0.4 inches. The flow of therapeutic fluid from the fluid reservoir 30 to the pump 32 may be aided by gravity.

Referring still to FIG. 1, the therapeutic fluid may flow from the pump 32 to a heater 34 disposed downstream of the pump 32. The therapeutic fluid may then flow through a system outlet line 26 to a patient inlet line 22 via a flow reversing valve (FRV) 12. The FRV 12 may include a first leg 14 fluidly coupled to the system outlet line 26 and disposed in a top portion 40 of the FRV 12. The system 10 may include a second leg 16 fluidly coupled downstream of the first leg 14 and upstream of a patient inlet line 22. Therapeutic fluid may then flow to a patient (not shown) via the patient inlet line 22, and back to the FRV 12 via a patient return line 24. Therapeutic fluid may flow back into the FRV 12 via a third leg 18 disposed downstream of the patient return line 24. From the third leg 18, fluid may flow to a fourth leg 20, then downstream to a system inlet line 28, and then eventually back to the fluid reservoir 30 downstream of the fourth leg 20. Each of the first and fourth legs 14, 20 may be disposed in the top portion 40 of the FRV 12 while each of the second and third legs 16, 18 may be disposed in a bottom portion 44 of the FRV 12. A retaining ring 46 may be used to secure the bottom portion 44 to the top portion 40 via threaded portions (not shown) on each of the top portion 40 and the bottom portion 44 (and/or via a compression fit).

Still referring to FIG. 1, the system 10 may include other components including (but not limited to) intravenous bag inlets disposed at the top of the fluid reservoir 30, intravenous bag stands, a vacuum source and one or more vacuum tubes, filters, vacuum relief valves, medication ports, other valves, pressure chambers, temperature probes, pressure probes, flow meters, as well as other components. In addition, the system 10 may include other arrangements of the various components (e.g., in other orders with respect to the flow of therapeutic fluid). Each of the patient inlet line 22 and the patient return 24 may include multiple lines (i.e., dual lumen lines, triple lumen lines, etc.) to allow for multiple access ports, as well as the simultaneous introduction of multiple medications (i.e., when medications are incompatible with each other, and thus cannot be premixed). Also illustrated in FIG. 1 is the flow of fluid 36 (e.g., therapeutic fluids such as blood, dialysate, and/or other lavage fluids) through the system. Note: the system 10 of FIG. 1 is not drawn to scale, but instead has been drawn such that annotations of the flow directions and system components may be visible.

Figure 1A:
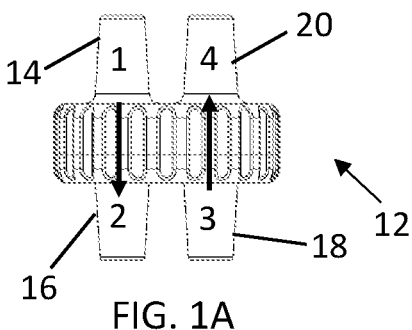
FIG. 1A illustrates a flow schematic of a first configuration of a patient treatment system according to aspects of the present embodiments.

FIG. 1A illustrates the direction of flow of each leg 14, 16, 18, 20 within the FRV 12 while it is in the first configuration. For example, in the first configuration embodied in FIG. 1, the first and second legs 14, 16 are in direct fluid communication such that fluid flow from the first leg 14 flows directly into the second leg 16. Similarly, in the first configuration, the third and fourth legs 18, 20 are in direct fluid communication such that fluid flow from the third leg 18 flows directly into the fourth leg 20.

Figure 2:
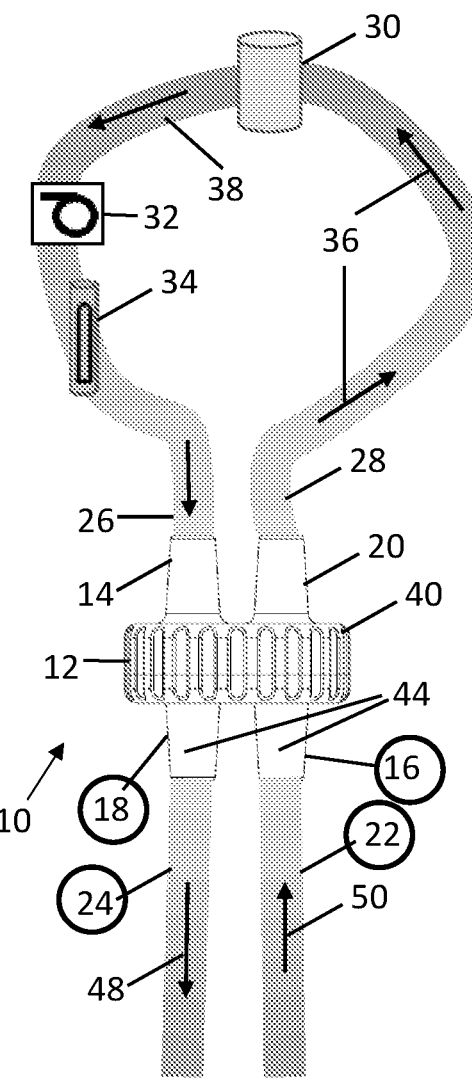
FIG. 2 illustrates a second configuration of a patient treatment system according to aspects of the present embodiment.

FIG. 2 illustrates a second configuration of a patient treatment system according to aspects of the present embodiment. In the embodiment of FIG. 2, the bottom portion 44 (along with the second and third legs 16, 18) has been rotated 180 degrees relative to the top portion 40. The embodiment of FIG. 2 may include all of the components of FIG. 1 including the FRV 12, the first, second, third, and fourth legs 14, 16, 18, 20, the fluid reservoir 30, the tubing 38, the pump 32, the heater 34, the system outlet line 26, the patient inlet line 22, the patient return line 24, and the system inlet line 28. As such, in the embodiment of FIG. 2, the first leg 14 is in direct fluid communication with the third leg 18 while the second leg 16 is in direct fluid communication with the fourth leg 20. (In the embodiment of FIG. 1, the first leg 14 is in direct fluid communication with the second leg 16 while the third leg 18 is in direct fluid communication with the fourth leg 20.) In the embodiment of FIG. 2, the fluid flow 36 around the system 10 is the same as that of FIG. 1. However, in the embodiment of FIG. 2, a first reverse flow 48 flows from the third leg 18, to the patient return line 24, and then to the patient (not shown). Similarly, in the embodiment of FIG. 2, a second reverse flow 50 flows from the patient (not shown), to the patient inlet line 22, to the second leg 16. Stated otherwise, in the embodiment of FIG. 2, fluid flows through both the patient inlet line 22 and the patient return line 24 in the opposite direction from the respective directions in the embodiment of FIG. 1. Note: the system 10 of FIG. 2 is not drawn to scale, but instead has been drawn such that annotations of the flow directions and system components may be visible. For example, the FRV 12 and the fluid lines 22, 24, 26, 28 may be drawn larger than their respective scaled dimensions while each of the fluid reservoir 30, pump 32, and fluid heater 34 may be drawn smaller than their respective scaled dimensions. In each of FIGS. 1 and 2, the element numbers corresponding to the second and third legs 16, 18, as well as the patient inlet and return lines 22, 24 have been circled to emphasize the differences between the first configuration of FIG. 1 and the second configuration of FIG. 2.

Figure 2A:
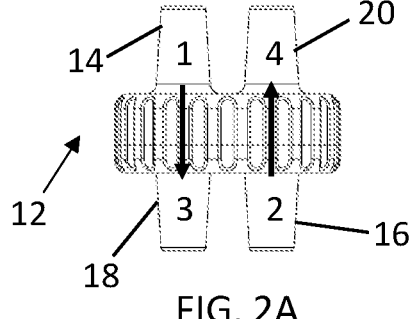
FIG. 2A illustrates a flow schematic of a second configuration of a patient treatment system according to aspects of the present embodiments.

FIG. 2A illustrates the direction of flow of each leg 14, 16, 18, 20 within the FRV 12 while it is in the second configuration. For example, in the second configuration embodied in FIG. 2, the first and third legs 14, 18 are in direct fluid communication such that fluid flow from the first leg 14 flows directly into the third leg 18. Similarly, in the second configuration, the second and fourth legs 16, 20 are in direct fluid communication such that fluid flow from the second leg 16 flows directly into the fourth leg 20.

In operation, the flow of fluid (such as blood, dialysate, therapeutic fluids and/or other lavage fluids) to and from the patient may be reversed by simply turning the bottom portion 44 through a rotation of 180 degrees relative to the top portion 40. The FRV 12 may be changed from the first position (illustrated in FIG. 1) to the second position (illustrated in FIG. 2) in less than a second. While the FRV 12 is transitioning from the first position to the second position, flow through the system 12 may continue; it is not necessary to stop pumping therapeutic fluid through the system while the FRV 12 is being switched from one position to the other and vice versa. Reversing flow within each of the patient inlet line 22 and the patient return line 24 allows debris and/or other clogged material to be removed and/or loosed from the system 10, thereby allowing for the free flow of therapeutic fluid. In addition, the FRV 12 may be switched from forward flow to reverse flow, then back to forward flow again within a few seconds, thereby clearing out blockages and/or debris while also minimizing the impact on the patient treatment regimen.

Flow Reversing Valve

FIG. 3 illustrates a top view of a flow reversing valve (FRV) 12 according to aspects of the present embodiments. In the embodiment of FIG. 3, the first leg 14 and the fourth leg 20 are both visible, both being disposed in a top surface 56 of the top portion 40. The top portion 40 may include a knurled circumference 48 making it easier to grip when switching the FRV 12 from one position to another position. The knurled circumference 48 may include alternating segments including outer portions 50, and curved inner portions 52. The curved inner portions 52 may be concave when viewed from the exterior. The outer portions 50 may be linear and/or planar. In other embodiments, the outer portions 50 may be both curved and concave (having a smaller radius of curvature than the curved inner portions 52). The outer portions 50 may also be cordial with the outer diameter of the top portion 40 and/or the retaining ring 46. In some embodiments, the knurled circumference 48 may include from about ten to about fifty alternating sections (i.e., from about ten to about fifty each of both the outer portions 50, and the curved inner portions 52). In some embodiments, the knurled circumference 48 may include from about fifteen to about forty alternating sections (i.e., from about fifteen to about forty each of both the outer portions 50, and the curved inner portions 52). In other embodiments, the knurled circumference 48 may include other numbers of alternating sections, as needed based on the dimensions of the FRV 12. In addition, the knurled circumference 48 may include other features other than the outer portions 50, and curved inner portions 52. For example, the knurled circumference 48 may include vertical linear grooves, notches, divots, convex curved portions, bumps, mounds, dimples, triangular knurls, diamond-shaped knurls, ridges, trenches, protuberances, combinations thereof, and/or other suitable features that allow the knurled circumference 48 to be gripped.

Referring still to FIG. 3, the FRV 12 may include one or more tapers 54 forming the transition between each of the first and fourth legs 14, 20 and the top surface 56 of the top portion 40. The one or more tapers 54 serve to both increase the flow area of the flow passage defined by each of the first and fourth legs 14, 20, as well as to increase the area over which each of the first and fourth legs 14, 20 is coupled to the top surface 56 of the top portion 40 (i.e., thereby enabling more robust connections between each of the first and fourth legs 14, 20 and the top surface 56 of the top portion 40). The increased flow area at each of the tapers 54 (i.e., at the interface between each of the first and fourth legs 14, 20 and the top surface 56 of the top portion 40) enhances the ability of the FRV 12 to make the various flow connections between the first, second, third, and fourth legs 14, 16, 18, 20 when the FRV 12 is in the first position (illustrated in FIG. 1) and the second position (illustrated in FIG. 2), as well as a third position (illustrated in FIGS. 12 and 13). Stated otherwise, the bases (or root portions) of each of the first and fourth legs 14, 20, which include increased diameters, aid the FRV 12 in making the desired fluid connections (i.e., fluidly connecting the first, second, third, and/or fourth legs 14, 16, 18, 20) because the increased flow area allows for increased overlap between flow passages. In some embodiments, the FRV 12 may also include tapers at the bases of each of the second and third legs 16, 18, thereby forming the transitions with the bottom portion 44 (shown in FIGS. 1, 2, and 7).

FIG. 4 illustrates a perspective view of a flow reversing valve 12 according to aspects of the present embodiments. The FRV 12 illustrated in FIG. 4 includes the knurled circumference 48 as well as first and fourth legs 14, 20 protruding from the top surface 56 of the top portion 40 at (or from) the respective tapers 54. In the embodiment of FIG. 4, one of the bottoms legs (either the third or fourth leg 16, 18 depending on whether the FRV 12 is in the configuration of FIG. 1 (with the fourth leg 20 in direct flow communication with the third leg 18) or in the configuration of FIG. 2 (with the fourth leg 20 in direct flow communication with the second leg 16)). The retaining ring 46 is also visible in the illustration of FIG. 4, along with a dividing line 58, which marks the interface between the top portion 40 and the retaining ring 46. Each of the first, second, third, and fourth legs 14, 16, 18, 20 may continue to taper from a root portion at the respective tapers 54 of each leg to a tip portion 60 of each leg. The taper from the root portion to the tip portion 60 allows each of the legs to have an increased diameter at the root, while allowing for a smaller diameter at the tip, where the connections to each of the flow lines 22, 24, 26, 28 (shown in FIGS. 1 and 2) are made.

FIG. 5 illustrates a front view of a flow reversing valve (FRV) 12 according to aspects of the present embodiments. In the embodiment of FIG. 5, the first and second legs 14, 16, as well as the third and fourth legs 18, 20 are in direct fluid communication (similar to the embodiment of FIG. 1). In the embodiment of FIG. 5, the FRV may include one or more detents 61 attached to the bottom portion 44. In connection with one or more stops 63, 65 coupled to the top portion 40, the one or more detents 61 may be used to prevent the rotation of the bottom portion 44 from exceeding 180 degrees. For example, as the bottom portion 44 is quickly rotated from a forward flow configuration (FIG. 1) to a reverse flow configuration (FIG. 2), the one or more detents 61 will rotate with the bottom portion 44 and contact the second stop 65 just as the rotation of the bottom portion 44 has reached 180 degrees. Similarly, as the bottom portion 44 is quickly rotated from a reverse flow configuration (FIG. 2) back to a forward flow configuration (FIG. 1), the one or more detents 61 will rotate back with the bottom portion 44 and contact the first stop 63 just as the rotation of the bottom portion 44 is returning to zero (0) degrees. In other embodiments, the detents 61 and the stops 63, 65 may not actually prevent rotation of the bottom portion 44 past one-hundred and eighty (180) degrees, but instead may help to establish where the flowpaths (i.e., within the top and bottom portions 40, 44) are aligned (while still allowing for 360-degree rotation of the bottom portion 44 relative to the top portion 40). In embodiments in which the detents 61 and the stops 63, 65 do not prevent rotation of the bottom portion 44 past one-hundred and eighty (180) degrees, there may not be any vertical overlap between the one or more detents 61 and the stops 63, 65, in which case the one or more detents 61 and the stops 63, 65 may simply be lined up when the FRV is rotated to the desired position, thereby ensuring that the flowpaths within the FRV are properly aligned.

Referring still to FIG. 5, the one or more detents 61 may be coupled to the bottom portion 44 (and the first and second stops 63, 65 may be coupled to the top portion 40) via any suitable mechanisms such as (but not limited to) epoxy, glue, fusion, compression fit (for example, within one of the grooves or knurl features). The one or more detents 61 and first and second stops 63, 65 may also be integral with the respective bottom and top portions 46, 40. (For example, the one or more detents 61 and first and second stops 63, 65 may be printed-on features of the top and bottom portions 40, 44, in embodiments of the FRV 12 that are fabricated via additive manufacturing (i.e., 3D printing)). In the embodiment of FIG. 5, one or more detents extends vertically beyond the top of the bottom portion 44 such that a portion of it may contact the first and second stops 63, 65. In other embodiments, the first and second stops 63, 65 may extend vertically below the bottom of the top portion 40, in order to contact the one or more detents 61. In other embodiments, the stops 63, 65 may be coupled to the bottom portion 44 while the one or more detents 61 may be coupled to the top portion 40. In other embodiments, the one or more detents 61 and stops 63, 65 may be positioned such that they stop the rotation of the bottom portion 44 at ninety degrees and/or at other desired values. In other embodiments, the angle at which the rotation is stopped via the one or more detents 61 and stops 63, 65 may be adjustable. The one or more detents 61 and stops 63, 65 allow the bottom portion 44 of the FRV 12 to be quickly rotated to exactly the desired location, without having to fine tune and/or readjust the FRV 12, and eliminating the chances of the rotation of the bottom portion 44 from overshooting the intended angle of rotation.

FIG. 6 illustrates a side view of a flow reversing valve (FRV) 12 including the first, second, third, and/or fourth legs 14, 16, 18, 20, according to aspects of the present embodiments. Because it is a side view, only two of the four legs are visible. In the embodiment of FIG. 6, the FRV 12 may include a body portion 64 which is comprised of a portion of the top portion 40 and the retaining ring 46. The body portion 64, which consists of two parts, allows the top portion 40 and the retaining ring 46 to rotate relative to each other. The dividing line 58 between the top portion 40 and the retaining ring 46 may be closer to the bottom of the body portion 64, in order to allow for sufficient overlap between the top portion 40 and the bottom portion 44 (shown in FIG. 7) and/or the retaining ring 46. The sufficient overlap between the top portion 40 and the bottom portion 44 allows each of an upper lip 70 disposed in the bottom portion 44 (shown in FIG. 7), a bottom lip 68 also disposed in the bottom portion 44 (shown in FIG. 7), a race 72 also disposed in the bottom portion 44 (shown in FIG. 7), and a gasket 42 (shown in FIG. 7) to fit within the top portion 40, thereby providing a tight seal when the FRV 12 is assembled. For example, in some embodiments, the dividing line 58 may be located from about ten percent to about sixty percent of the height of the body portion 64. In other embodiments, the dividing line 58 may be located from about twenty percent to about fifty percent of the height of the body portion 64. In other embodiments, the dividing line 58 may be located from about thirty percent to about forty percent of the height of the body portion 64.

Referring still to FIG. 6, the FRV 12 may include one or more fillets and/or chamfers 62 around the circumferences of the top and bottom edges of the body portion 64. For example, each of the top portion 40 and retaining ring 46 may include edges with fillets and/or chamfers 62 disposed therein. The one or more detents 61 as well as the first stop 63 are also visible in FIG. 6. In the illustration of FIG. 6, the detent 61 is abutting the first top 63 indicating that the bottom portion 44 is rotated zero (0) degrees relative to the top portion 40.

Figures 7, 8, 9:
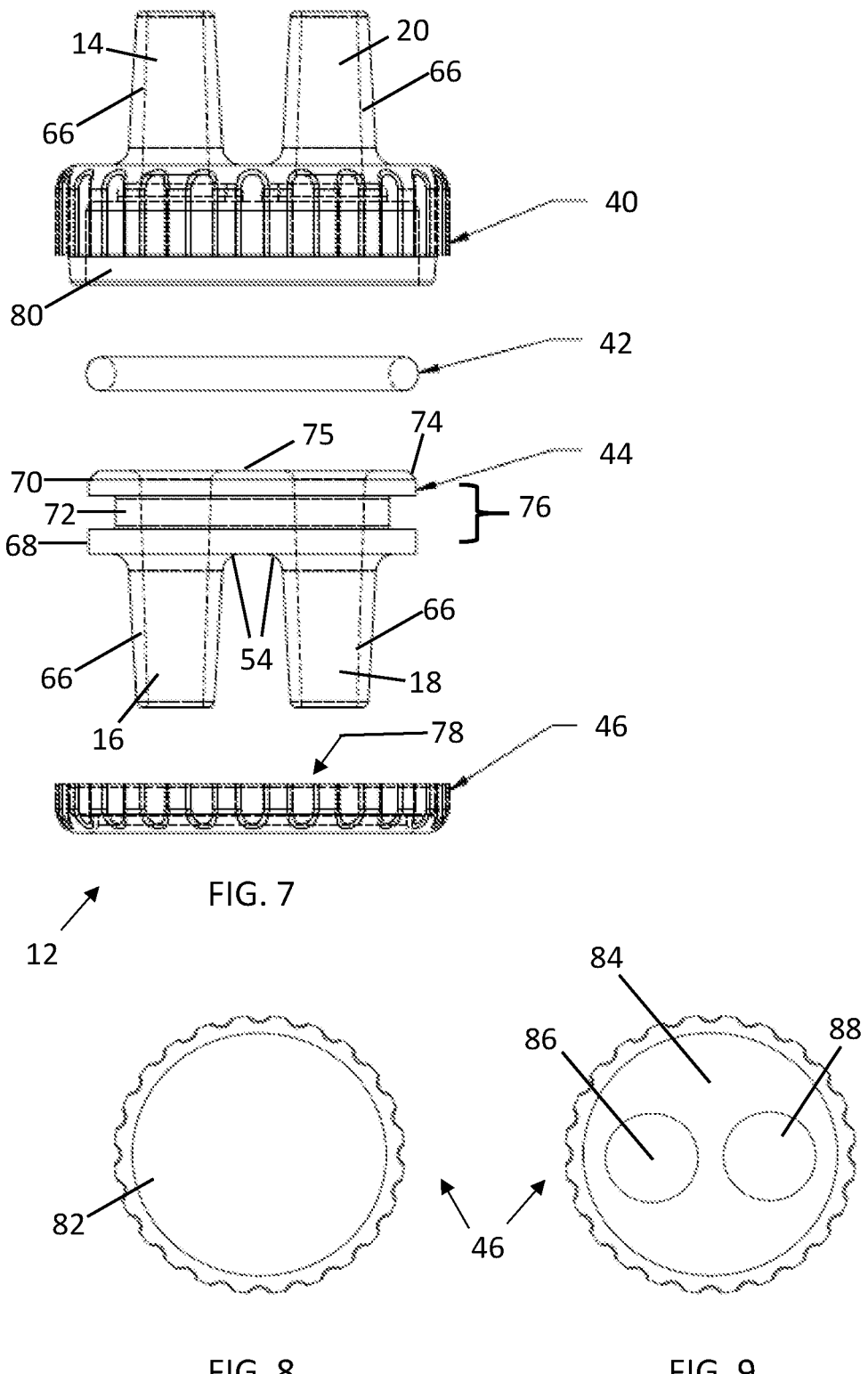
FIG. 7 illustrates a side view of a flow reversing valve assembly according to aspects of the present embodiments.
FIG. 8 illustrates a bottom view of a retaining ring according to aspects of the present embodiments.
FIG. 9 illustrates a bottom view of the retaining ring according to aspects of the present embodiments.

FIG. 7 illustrates a side view of a flow reversing valve (FRV) 12 assembly according to aspects of the present embodiments. The FRV 12 includes four components: the top portion 40, a gasket (or o-ring) 42, the bottom portion 44, and the retaining ring 46. FIG. 7 includes illustrations of flow passages 66 (illustrated with dashed lines) within each of the first, second, third, and fourth legs 14, 16, 18, 20. The gasket 42 may be stretched around an upper lip 70 of the bottom portion 44 such that it rests within a race 72 (or notch) of the bottom portion between the upper lip 70 and a bottom lip 68. Each of the top and bottom lips 70, 68 include a larger diameter than the race 72. Once the gasket 42 is placed around the race 72, the bottom portion 44 may be inserted within a female fitting 80 disposed at the bottom of the top portion 40. In particular, a male fitting 76 of the bottom portion 44 which comprises the upper lip 70, the race 72, and the bottom lip 68 may be inserted into the female fitting 80 extending downward from the bottom of the top portion 40. As such, each of the top and bottom lips 70, 68 may be sized such that their respective outer diameters (which themselves may be approximately equal) are approximately the same size as an inner diameter of the female fitting 80 (recognizing that after allowing for tolerances, the outer diameter of each of the top and bottom lips 70, 68 will resultantly be slightly smaller than the inner diameter of the female fitting 80).

Referring still to FIG. 7, the gasket 42 may be sized so that the thickness of the gasket 42 extends slightly past the outer diameters of each of the top and bottom lips 70, 68. As such, when the male fitting 76 is inserted into the female fitting 80, the gasket 42 will need to compress in order to fit, thereby creating a robust compression fit that also ensures an adequate fluid seal. Because the gasket 42 should have the ability to flex, stretch, and/or compress, it may be composed of a softer and/or more flexible material than the top and/or bottom portions 40, 44. For example, the gasket 42 may be composed of a material with a Young's modulus from about 0.001 Mpsi to about 0.2 Mpsi while each of the top and bottom portions 40, 44 may be composed of polymer and/or thermoplastic materials with a Young's modulus from about 0.15 Mpsi to about 0.6 Mpsi. In other embodiments, it may be desirable for each of the top and bottom portions 40, 44 as well as the retaining ring 46 to be composed of a metallic material (for example, if a course of treatment entails introducing substances to the therapeutic fluid that detrimentally interact with materials with lower Young's moduli (and/or chemically interacts with polymer compositions), or if some therapeutic benefit can be achieved by passing the therapeutic fluid through a metallic FRV 12). In such embodiments, the top and bottom portions 40, 44 as well as the retaining ring 46 may be composed of materials with a Young's modulus above about 1.0 Mpsi while the gasket 42 may be composed of materials with a Young's modulus from about 0.001 Mpsi to about 0.6 Mpsi. The bottom portion 44 may also include a fillet and/or chamfer 74 at the transition between the upper lip 70 and a top surface 75 of the bottom portion 44.

Still referring to FIG. 7, and also FIGS. 8 and 9, once the male fitting 76 (with the gasket 42 disposed thereon) is within the female fitting 80, the retaining ring 46 may be brought around the bottom portion 44 such that an inner lip 78 of the retaining ring 46 interfaces with the outer surface of the female fitting 80. In a first embodiment, female threads (not shown) on the inner lip 78 of the retaining ring 46 may engage male threads (not shown) on the outer surface of the female fitting 80. In this first embodiment, the retaining ring 46 may include a hollow center 82 (as illustrated in FIG. 8) such that the bottom portion 44 may rotate therewithin (i.e., to switch the position of the FRV 12) once the retaining ring 46 has been screwed onto the top portion 40. In a second embodiment, neither the inner lip 78 of the retaining ring 46 nor the outer surface of the female fitting 80 includes threads and the retaining ring 46 instead slides over the female fitting 80, creating a secure coupling via compression fit. In this second embodiment (as illustrated in FIG. 9), the retaining ring 46 may include first and second holes 86, 88 disposed within a bottom surface 84 of the retaining ring 46, allowing the second and third legs 16, 18 to fit therethrough. In the first embodiment (FIG. 8) the retaining ring 46 does not rotate with the bottom portion 44 because it is screwed onto the top portion 40. In contrast to the first embodiment, in the second embodiment (FIG. 9), the retaining ring 46 does rotate with the bottom portion 44. In both embodiments, once assembled, the female fitting 80 is disposed both radially outward of the male fitting 76, and radially inward of the retaining ring 46. FIG. 7 also illustrates tapers 54 disposed in the bottom portion 44. (The tapers 54 on the bottom portion 44 are not visible in the illustrations of FIGS. 5 and 6 because they are covered up by the retaining ring 46). In a third embodiment (similar to the first embodiment in the sense that the retaining ring 46 remains fixed to the top portion 40 while the bottom portion 44 rotates therewithin), the retaining ring 46 may be attached onto the female fitting 80 via solvent bonding, adhesive bonding, ultrasonic welding, fusion, epoxy, as well as other suitable attachment and/or joining mechanisms. In other embodiments, the retaining ring 46 may be integral with the bottom portion 44 and may fit together with the gasket 42 and top portion 40 via compression fit and/or other suitable mechanisms such as via a snap fit and/or quick connect.

Figure 10:
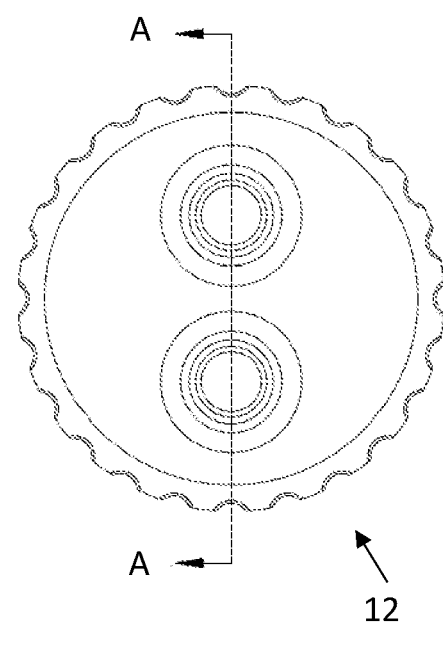
FIG. 10 illustrates a top view of a flow reversing valve according to aspects of the present embodiments.

FIG. 10 illustrates a top view of a flow reversing valve (FRV) 12 according to aspects of the present embodiments and including a cut-line A-A.

Figure 11:
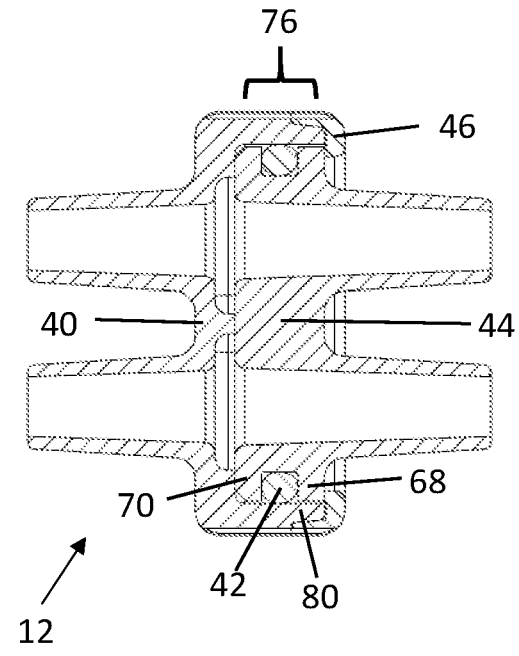
FIG. 11 illustrates a cross-sectional view of a flow reversing valve according to aspects of the present embodiments.

FIG. 11 illustrates a cross-sectional view of a flow reversing valve (FRV) 12 according to aspects of the present embodiments taken at the cut-line A-A of FIG. 10. The illustration of FIG. 11 details the assembled FRV 12 including: the gasket 42 disposed around the bottom portion 44 between the upper lip 70 and the bottom lip 68; the male fitting 76 inserted into the female fitting 80; and the retaining ring 46 engaged with the female fitting 80 (via threads and/or compression fit) which is disposed at the bottom of the top portion 40.

Figure 12:
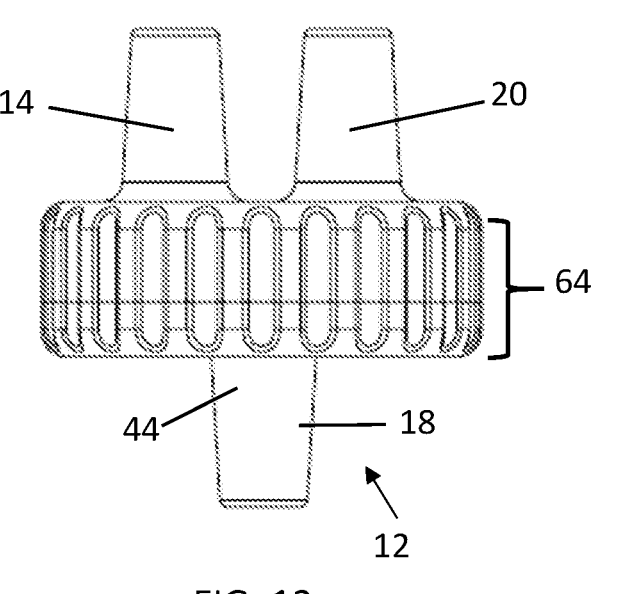
FIG. 12 illustrates a front view of a flow reversing valve in a third configuration according to aspects of the present embodiments.

FIG. 12 illustrates a front view of a flow reversing valve (FRV) 12 in a third configuration according to aspects of the present embodiments. In the embodiment of FIG. 12, the bottom portion 44 has been rotated clockwise (when viewed from the top) 90 degrees within the body portion 64 relative to the configuration of FIG. 1. In the embodiment of FIG. 12, the first, third and fourth legs 14, 18, 20 are visible while the second leg 16 is behind the third leg 18 (and thus not visible).

Figure 13:
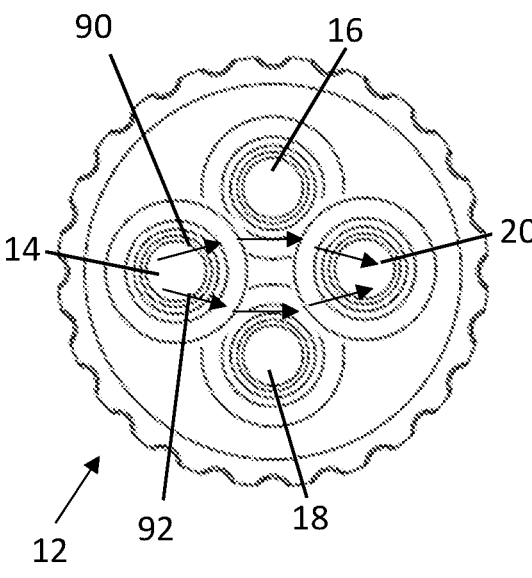
FIG. 13 illustrates a top view of a flow reversing valve in a third configuration according to aspects of the present embodiments.

FIG. 13 illustrates a top view of a flow reversing valve (FRV) 12 in a third configuration according to aspects of the present embodiments. FIG. 13 is a top view of the embodiment of FIG. 12 in which the bottom portion 44 has been rotated clockwise (when viewed from the top) 90 degrees from the configuration of FIG. 1. In the third configuration (i.e., with the bottom portion 44 rotated 90 degrees) the flow passage of the first leg 14 partially overlaps with the flow passages of the second and third legs 16, 18, which in turn both partially overlap with the flow passage of the fourth leg 20. Thus, in the third configuration, fluid may follow two different paths to flow from the first leg 14 to the fourth leg 20. Following the first path 90, fluid flows from the first leg 14 into at least the tapered portion of the second leg 16, and then from the second leg 16 into the fourth leg 20. Following a second path 92, fluid flows from the first leg 14 into at least the tapered portion of the third leg 18, and then from the third leg 18 into the fourth leg 20. The third configuration essentially acts as a patient bypass since fluid will take the path of least resistance and flow from the first leg 14 directly into the fourth leg 20, rather than flowing all the way through the patient inlet line 22, through the circulation system internal to the patient, and finally through the patient return line 24 to reach the fourth leg 20. An additional benefit of the bypass mode is that pressure spikes (associated with suddenly cutting off flow downstream of the pump 32) are avoid since the flow lines are continuously fluidly connected to one or more downstream lines. Stated otherwise, in bypass mode, the outlet flow from the pump 32 that bypasses the patient system is never fully obstructed, even if the valve is turned slowly. As such, pump alarms (which may cause the pump 32 to stop pumping entirely) may be avoided since the bypass modes (through which the FRV 12 passes while it is being rotated from forward flow to reverse flow modes of operation and vice versa) eliminate pressure spikes (which typically may cause pump alarms and subsequent pump shut-offs).

Referring still to FIG. 13, which illustrates a 90-degree rotation of the bottom portion 44, the flow passages may still overlap if the rotation is not exactly 90 degrees. For example, if the rotation is from about 85 degrees to about 95 degrees, there is expected to be flow passage overlap (and thus fluid communication) between the first leg 14 and both the second and third legs 16, 18, as well as between both the second and third legs 16, 18 and the fourth leg 20. Similarly, if the rotation is from about 80 degrees to about 100 degrees, there is expected to be flow passage overlap (and thus fluid communication) between the first leg 14 and both the second and third legs 16, 18, as well as between both the second and third legs 16, 18 and the fourth leg 20. However, from about an 80-degree rotation to about a 70-degree rotation (and similarly from about a 100-degree rotation to about a 110-degree rotation), the flow communication begins to peter out such that at rotations of about 70 degrees and about 110 degrees there is no (or virtually no) flow passage overlap or fluid communication between the first and fourth legs 14, 20 (i.e., via the second and third legs 16, 18). With respect to forward flow (i.e., corresponding to the first configuration of FIG. 1) rotations of zero (0) degrees+/−60 degrees are expected to produce only forward flow (with less flow restriction occurring the closer you get to 0 degrees). With respect to reverse flow (i.e., corresponding to the second configuration of FIG. 2) rotations of 180 degrees+/−60 degrees (i.e., rotations of about 120 degrees to about 240 degrees) are expected to produce only reverse flow (with less flow restriction occurring the closer you get to 180 degrees). For example, in one embodiment, rotations of about 150 degrees to about 210 degrees may provide the desired reverse flow rates. In another embodiment, rotations of about 165 degrees to about 195 degrees may provide the desired reverse flow rates. Accordingly, in each of the three configurations (forward flow, reverse flow, and patient bypass mode) a range of rotation angles are possible. In addition, the FRV 12 provides a way of controlling the flow rate by adjusting the flow restriction via the angle of rotation of the bottom portion 44, as discussed above.

Figure 14:
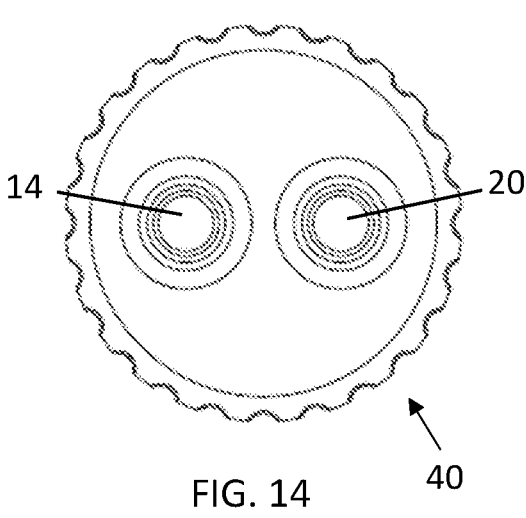
FIG. 14 illustrates a top view of a portion of a flow reversing valve according to aspects of the present embodiments.
Figure 15:
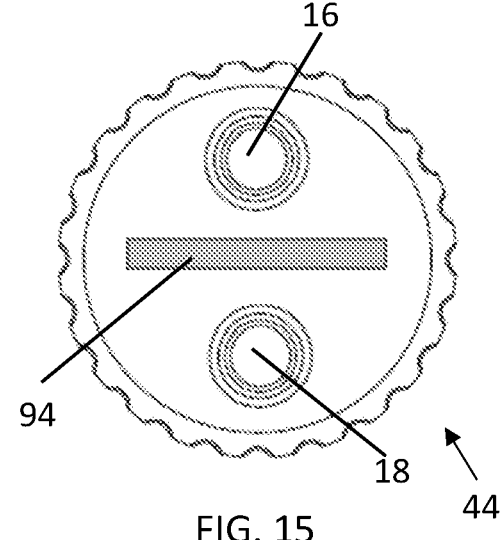
FIG. 15 illustrates a top view of a portion of a flow reversing valve according to aspects of the present embodiments.

FIGS. 14-17 illustrate two additional embodiments for creating bypass modes within the FRV 12. FIGS. 14 and 15 correspond to the first additional embodiment while FIGS. 16 and 17 correspond to the second additional embodiment.

Referring to FIGS. 14 and 15, FIG. 14 illustrates a top view of the top portion 40 while FIG. 15 illustrates a bottom view of the bottom portion 44, according to aspects of the present embodiments. The bottom portion 44 has been rotated 90 degrees and includes a center trough 94 which allows the first and fourth legs 14, 20 to fluidly communicate when the FRV 12 is assembled (and rotated 90 degrees). In this first additional embodiment, fluid bypasses the patient.

Figure 16:
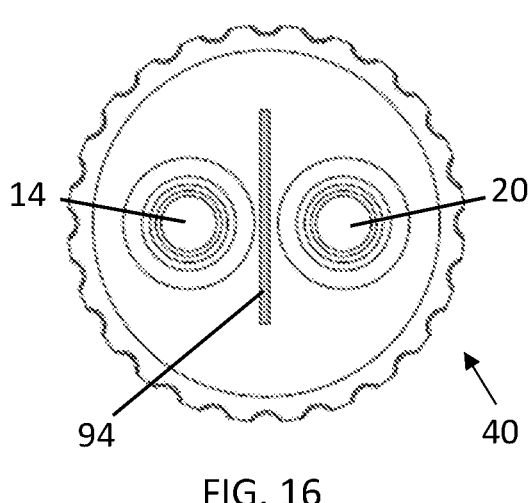
FIG. 16 illustrates a top view of a portion of a flow reversing valve according to aspects of the present embodiments.
Figure 17:
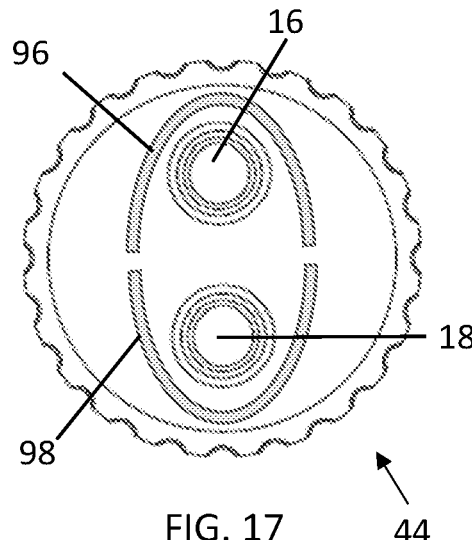
FIG. 17 illustrates a top view of a portion of a flow reversing valve according to aspects of the present embodiments.

Referring to FIGS. 16 and 17, FIG. 16 illustrates a top view of the top portion 40 while FIG. 17 illustrates a bottom view of the bottom portion 44, according to aspects of the present embodiments. The top portion 40 includes a center trough 94 disposed therein which serves to fluidly couple the second and third legs 16, 18 when the bottom portion 44 is rotated 90 degrees (and the FRV is assembled). The bottom portion 44 has been rotated 90 degrees and includes a first curved passage 96 as well as a second curved passage 98 disposed therein. Each of the first and second curved passages 96, 98 allows the first and fourth legs 14, 20 to fluidly communicate when the FRV 12 is assembled (and the bottom portion 44 is rotated 90 degrees). In this second additional embodiment, fluid at the top portions of the embodiments of FIGS. 1 and 2 bypasses the patient. However, in this second additional embodiment, the patient inlet line 22 and the patient return line 24 are also in fluid communication allowing the fluid (for example, blood, dialysate, therapeutic fluids and/or other lavage fluids) to continue to circulate around the patient's system. In each of the embodiments of FIGS. 14-17, it may be desired for at least one or two of the flow passages within the first, second, third, and fourth legs 14, 16, 18, 20 to be smaller, since the bypass mode is achieved via the center trough 94 and/or via the first and second curved passages 96, 98 rather than via overlapping passages. For example, the flow passages corresponding to the second and third legs 16, 18 in both FIGS. 15 and 17 are illustrated as having smaller diameters than the flow passages corresponding to the first and fourth legs 14, 20 in FIGS. 14 and 16. The smaller flow passages of FIGS. 15 and 17 also allow there to be more space available in the bottom portion 44 for inclusion of the center trough 94 and/or the first and second curved passages 96, 98. The center trough 94 disposed in the top portion as well as the first and second curved passages 96, 98 disposed in the bottom portion 44 are all sized and shaped such that they do not intersect to avoid flow communication therebetween (i.e., they do not intersect when the bottom portion is at zero (0) degrees, 90 degrees and/or 180 degrees).

The FRV 12 may be composed of any suitable materials include polymers, plastics, thermoplastics, polyether ether ketone (PEEK), rubber, nylon, metals, ceramics, composite materials, and/or other suitable materials. As discussed above, it may be desirable for the gasket 42 to be composed of a material with a lower Young's modulus than that of the top portion 40, the bottom portion 44, and the retaining ring 46. Each of the gasket 42, top portion 40, bottom portion 44, and the retaining ring 46 may be fabricated via any suitable means such as additive manufacturing (3D printing), invest-ment casting, injection molding, rapid prototyping, hybrid methods (such as additive manufacturing followed by at least one subtractive step such as drilling, cutting, grinding, and/or milling), as well as other suitable methods. If fabri-cated via additive manufacturing, the FRV 12 may be made via any acceptable method or modality such as (but not limited to) fused deposition modeling (FDM), stereo-lithog-raphy (SLA), binder jet, digital laser processing (DLP), selective laser sintering (SLS), selective laser melting (SLM), direct metal laser melting (DMLM), direct metal laser sintering (DMLS), electron beam melting (EBM), as well as other methods and/or modalities.

Methods

Figure 18:
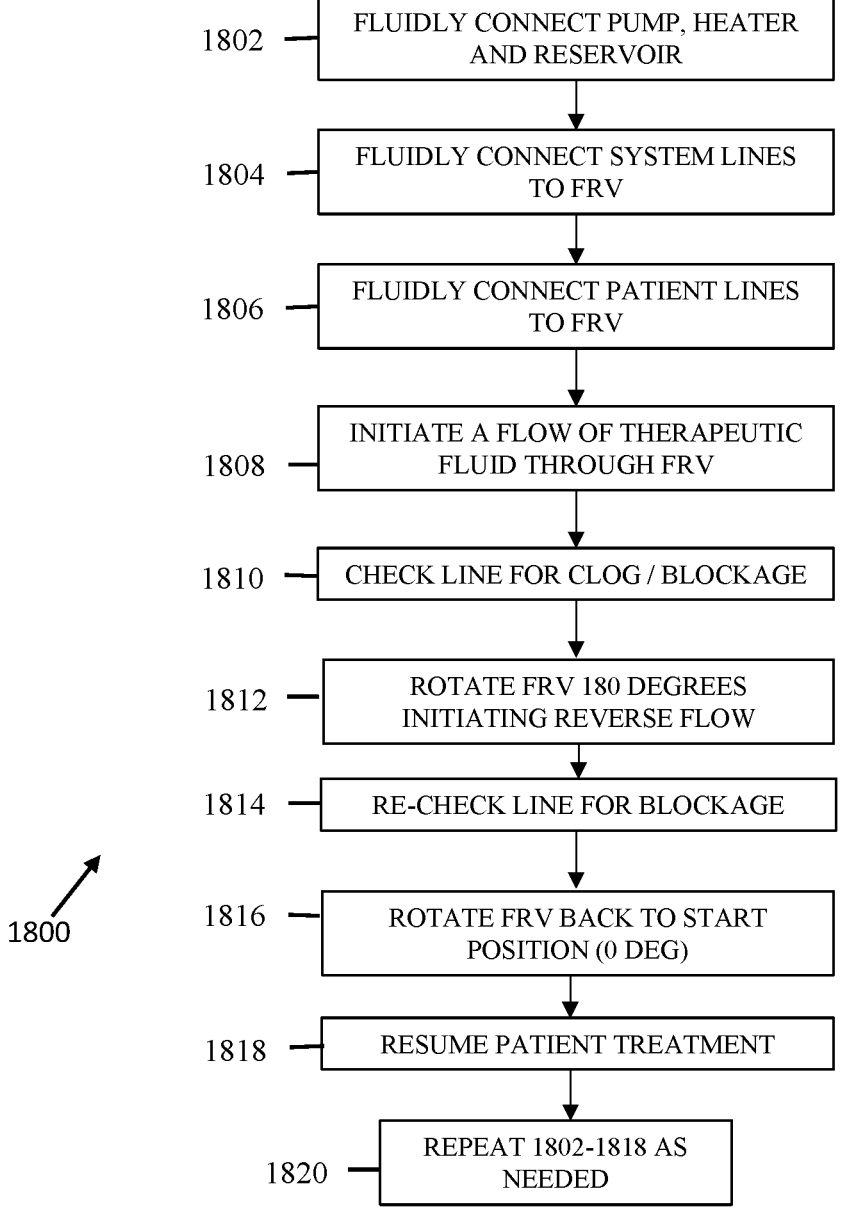
FIG. 18 illustrates a method of treating a patient, in accordance with aspects of the present disclosed embodiments.

FIG. 18 illustrates a method 1800 of treating a patient, in accordance with aspects of the present embodiments. At step 1802, the method 1800 may include fluidly connecting a pump 32, heater 34, fluid reservoir 30, and/or other com-ponents to the system. At steps 1804 and 1806, the method 1800 may include fluidly connecting the FRV 12 to the system (i.e., connecting the patient inlet and returns lines 22, 24 as well as the system inlet and outlet lines 28, 26 to the first, second, third, and/or fourth legs 14, 16, 18, 20). At step 1808, the method 1800 may include initiating a flow of therapeutic fluid through the FRV 12 (as well as through the fluid reservoir 30, pump 32, heater 34, and/or other system components). At step 1810, the method 1800 may include checking at least one line (such as the patient inlet line 22 and/or the patient return line 24) for clogs, blockages, and/or debris. At step 1812, the method 1800 may include rotating the FRV 12 about one-hundred and eighty (180) degrees such that a reverse flow is initiated in at least one line (such as the patient inlet line 22 and/or the patient return line 24). At step 1814, the method 1800 may include re-checking at least one line (such as the patient inlet line 22 and/or the patient return line 24) for clogs, blockages, and/or debris (for example, to see if the reverse flow operation was effective at removing the debris, clog and/or blockage.

Referring still to FIG. 18, at step 1816, the method 1800 may include rotating the FRV 12 back to the start position (i.e., at zero (0) degrees), thereby re-initiating forward flow operation. At step 1818, the method 1800 may include resuming one or more patient treatments (which may include fluid heating, IV injection, dialysis, and/or other therapeutic steps). At step 1820, the method 1800 may include repeating any of steps 1802-1818 as many time as needed. Steps 1802-1820 may be performed in a different order than what it shown in FIG. 18, and one or more steps may be omitted. In addition, steps not illustrated in FIG. 18 (including steps of method 1900 illustrated in FIG. 19) may also be included in method 1800.

Figure 19:
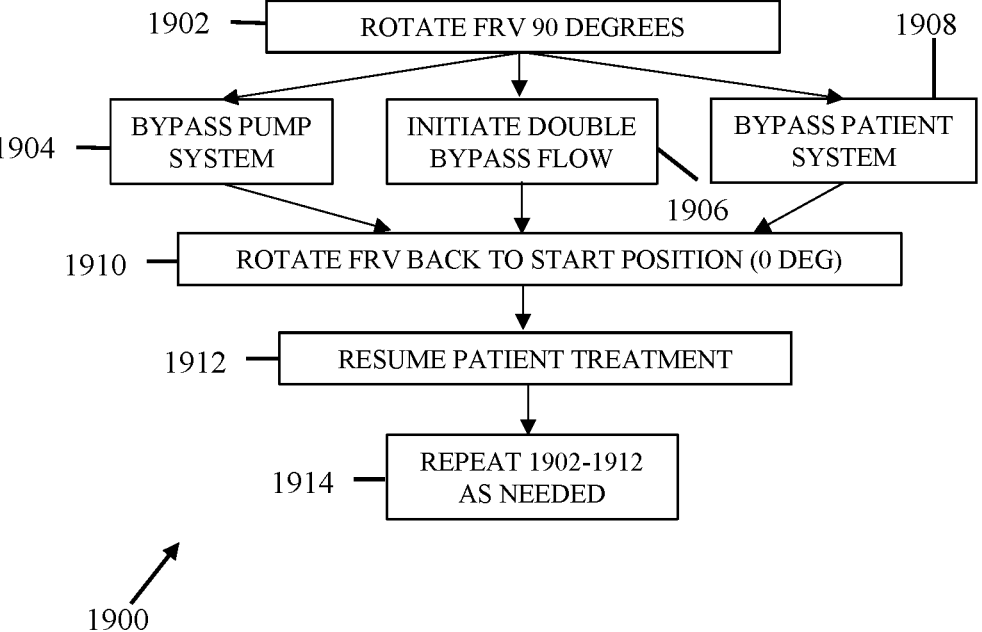
FIG. 19 illustrates a method of treating a patient, in accordance with aspects of the present disclosed embodiments.

FIG. 19 illustrates a method 1900 of treating a patient, in accordance with aspects of the present embodiments. At step 1902, the method 1900 may include rotating the FRV 12 ninety (90) degrees, thereby initiating one or more bypass modes of operation within the FRV 12. At step 1904, the method 1900 may include bypassing the pump system (i.e., to replace a component such as the fluid reservoir 30, the pump 32, the heater 34, and/or another component, or to replenish a consumable such as intravenous fluid, dialysate, therapeutic fluid, one or more filters, and/or other consum-ables). At step 1906, the method 1900 may include initiating a double bypass flow mode (similar to the embodiments of FIGS. 16 and 17) in which the patient inlet line 22 is in direct fluid communication with the patient return line 24, and in which the system outlet line 26 is in direct communication with the system inlet line 28. At step 1908, the method 1900 may include bypassing the patient (similar to the embodi-ments of FIGS. 12-15), for example, if the patient needs to take a temporary break from treatment but benefits from remaining fluidly connected to the system.

Referring still to FIG. 19, steps 1904, 1906, and 1908 include three different bypass modes. These steps can be performed separately, in series, and/or omitted as needed. At step 1910, the method 1900 may include rotating the FRV 12 back to the start position (i.e., at zero (0) degrees) thereby re-initiating forward flow. At step 1912, the method 1900 may include resuming a patient treatment. At step 1914, the method 1900 may include repeating any of steps 1902-1912, as many times as needed. Steps 1902-1910 may be per-formed in a different order than what it shown in FIG. 19, and one or more steps may be omitted from method 1900. In addition, steps not illustrated in FIG. 19 (for example, the steps of method 1800 illustrated in FIG. 18) may also be included in method 1900. Both methods 1800, 1900 may be performed concurrently with a patient treatment, or alterna-tively, may be performed in the absence of a concurrent patient treatment (i.e., to remove a clog or blockage from one or more system lines).

The systems 10, methods 1800, 1900 and flow reversing valve 12 of the present disclosed embodiments allow a flow of therapeutic fluid through at least portions of the system 10 to be reversed without needing to disconnect any portion of the system 10. By reversing the direction of flow within one or more portions of the system (even temporarily), block-ages, clogs and debris may be removed from the system 10, while subjecting the patient to only a very brief pause in treatment. Moreover, the systems 10, methods 1800, 1900, and flow reversing valve 12 of the present disclosed embodi-ments allow for flow bypassing of one or more components in the system, including the double-bypassing of multiple flow circuits simultaneously. By initiating one or more bypass modes, components of the system may be replaced, taken offline, brought online, serviced, and/or repaired, without requiring that the patient be disconnected from the system. In addition, in bypass mode, a patient treatment regimen can be temporarily paused without requiring any disconnections from the system. The forward flow, reverse flow and bypass flow modes can be initiated in a fraction of a second by rotating the bottom portion 44 of the flow reversing valve 12, without needing to disconnect any lines or even stop the flow of fluid through the system. Moreover, the FRV 12 allows the system to achieve reverse flow in portions of the system (for example, in the patient system) while maintaining forward fluid in other portions of the system (for example, in the pump system).

The present embodiments have been described primarily in terms of patient treatment systems where reversing flow in one or more portions of the system can aid in removing blockages and/or debris. The present embodiments may also aid in bypassing portions of a system without having to disconnect one or more components or fluid lines. The present embodiments may also be utilized in other indus-tries. For example, in the automotive industry, various fluid systems (such as (but not limited to) oil in the lubrication system, transmission fluid in the transmission, brake fluid, washer fluid, coolant and/or water in the radiator, hydraulic fluid in vehicles with hydraulic systems, as well as other fluid systems) may also become clogged with debris, coking, viscosity breakdown, deposits, and/or other forms of fluid degradation and may require removable of these clogs. Since many of these fluids are replaced at regular intervals, using the flow reversing valve (FRV) 12 of the present embodiments would allow for temporary reverse flow operation while the fluids are being replaced, thereby aiding in the removal of debris and blockages without requiring much extra effort or time. Other types of vehicles such as trains, aircraft, boats, and/or motorcycles as well as refrigeration and HVAC equipment could similarly benefit from integration of the flow reversing valve (FRV) 12 of the present embodiments into the various associated maintenance systems and tooling of those systems.

Certain Definitions

In order for the present disclosure to be more readily understood, certain terms are first defined below. Additional definitions for the following terms and other terms are set forth throughout the specification.

As used herein, the term "administration" refers to the administration of a composition to a subject or system. Those of ordinary skill in the art will be aware of a variety of routes that may, in appropriate circumstances, be utilized for administration to a subject, for example a human. For example, in certain embodiments, In some particular embodiments, administration A composition, apparatus, or method described herein as "comprising" one or more named elements or steps is open-ended, meaning that the named elements or steps are essential, but other elements or steps may be added within the scope of the composition or method. To avoid prolixity, it is also understood that any composition, apparatus, or method described as "comprising" (or which "comprises") one or more named elements or steps also describes the corresponding, more limited composition, apparatus, or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition, apparatus, or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition, apparatus, or method disclosed herein, known or disclosed equivalents of any named essential element or step may be substituted for that element or step.

As used herein, the term "patient" or "subject" (used interchangeably herein) refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In certain embodiments, a patient is a human. In certain embodiments, a patient is suffering from or susceptible to one or more disorders or conditions. In certain embodiments, a patient displays one or more symptoms of a disorder or condition. In certain embodiments, a patient has been diagnosed with one or more disorders or conditions. In certain embodiments, the disorder or condition is or includes bacterial infection. In certain embodiments, the patient is receiving or has received certain therapy to diagnose and/or to treat a disease, disorder, or condition.

As used herein, the term "substantially" refers to the qualitative condition of exhibiting total or near-total extent or degree of a characteristic or property of interest.

As used herein, the term "treatment" (also "treat" or "treating") refers to any administration of a therapy

EQUIVALENTS

It is to be understood that while the disclosure has been described in conjunction with the detailed description thereof, the foregoing description is intended to illustrate and not limit the scope of the invention(s). Other aspects, advantages, and modifications are within the scope of the claims.

This written description uses examples to disclose the invention, including the best mode, and also to enable any person skilled in the art to practice the present embodiments, including making and using any devices or systems and performing any incorporated methods. The patentable scope of the present embodiments is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A flow reversing valve comprising:
   a top portion;
   a retaining ring coupled to the top portion, the retaining ring being a separate component from the top portion;
   a bottom portion at least partially disposed between the top portion and the retaining ring, the bottom portion and the retaining ring both being rotatable relative to the top portion when assembled therewith;
   a gasket radially disposed around the bottom portion, the gasket at least partially disposed between the top portion and the bottom portion such that the gasket is disposed radially outward of the bottom portion and radially inward of the top portion,
   a first leg disposed within the top portion;
   a second leg disposed within the bottom portion;
   a third leg disposed within the bottom portion; and
   a fourth leg disposed within the top portion,
   wherein a first rotation of the bottom portion relative to the top portion causes flow in at least one portion of the flow reversing valve to reverse direction,
   wherein at least one of the top portion and the bottom portion comprises a trough disposed therein,
   wherein the trough comprises a center trough that fluidly connects the first leg to the fourth leg when the bottom portion is rotated about 90 degrees relative to the top portion, the center trough linearly extending through a center of the top portion or the bottom portion and comprising only a rectangular-shaped trough, and wherein both the top portion and the retaining ring comprise a knurled circumference.

2. The valve of claim 1, wherein the first leg is fluidly coupled directly to the second leg before the first rotation, and
   wherein the third leg is fluidly coupled directly to the fourth leg before the first rotation.

3. The valve of claim 1, wherein the first leg is fluidly coupled directly to the third leg after the first rotation, and
   wherein the second leg is fluidly coupled directly to the fourth leg after the first rotation.

4. The valve of claim 1, wherein both the top portion and the retaining ring comprise a knurled circumference.

5. The valve of claim 1, wherein at least one of the first leg, the second leg, the third leg, and the fourth leg comprises at least one taper at a transition with the respective top portion and/or bottom portion.

6. The valve of claim 1, wherein the first rotation is from about 165 degrees to about 195 degrees.

7. The valve of claim 6, wherein a second rotation of from about 80 degrees to about 100 degrees of the bottom portion relative to the top portion causes at least one fluid flow to bypass at least one portion of the flow reversing valve.

8. The valve of claim 1, wherein the bottom portion further comprises:

an upper lip;

a lower lip disposed beneath the upper lip; and a race disposed between the upper lip and the lower lip, the race comprising a smaller diameter than each of the upper lip and the lower lip, wherein the gasket is disposed around the race between the upper lip and the lower lip.

9. The valve of claim 1, further comprising:

at least one detent coupled to at least one of the top portion and the bottom portion; and at least one stop coupled to at least one of the top portion and the bottom portion, wherein the at least one detent contacts the at least one stop at a rotation of at least one of zero (0) degrees, ninety (90) degrees, and one-hundred and eighty (180) degrees.

10. The valve of claim 9, wherein the valve consists of the top portion, the bottom portion, the retaining ring, and the gasket.

11. The valve of claim 10, wherein each of the top portion, the bottom portion, the retaining ring, and the gasket comprises a single, separate piece that is separable from the remaining three pieces of the four total pieces forming the valve.

12. The valve of claim 1, wherein the gasket is composed of a first material, wherein each of the top portion, the bottom portion and the retaining ring are composed of one or more second materials, and wherein a Young's modulus of the first material is less than a Young's modulus of the one or more second materials.

13. The valve of claim 1, the top portion comprising a female fitting disposed at a bottom of the top portion; and the bottom portion comprising a male fitting disposed at a top of the bottom portion, wherein the male fitting is inserted into the female fitting, wherein the female fitting is disposed radially outward of the male fitting, wherein the female fitting is disposed radially inward of the retaining ring, and wherein the retaining ring is coupled to the top portion via a compression fit.

14. The valve of claim 1, wherein, when assembled, the top portion is in direct contact with the retaining ring.

15. The valve of claim 1, wherein the bottom portion is a separate component from the retaining ring.

16. The valve of claim 1, wherein the valve comprises an assembly of exactly four components, the exactly four components comprising the top portion, the bottom portion, the retaining ring, and the gasket.

17. The valve of claim 2, wherein the retaining ring comprises a first hole and a second hole, each of the first hole and the second hole disposed within a bottom surface of the retaining ring, and wherein, when the valve is assembled:

the second leg extends through the first hole; and the third leg extends through the second hole.

18. A flow reversing valve comprising:

a top portion;

a retaining ring coupled to the top portion, the retaining ring being a separate component from the top portion;

a bottom portion at least partially disposed between the top portion and the retaining ring, the bottom portion and the retaining ring both being rotatable relative to the top portion when assembled therewith;

a gasket radially disposed around the bottom portion, the gasket at least partially disposed between the top portion and the bottom portion such that the gasket is disposed radially outward of the bottom portion and radially inward of the top portion, a first leg disposed within the top portion;

a second leg disposed within the bottom portion;

a third leg disposed within the bottom portion; and a fourth leg disposed within the top portion, wherein a first rotation of the bottom portion relative to the top portion causes flow in at least one portion of the flow reversing valve to reverse direction, wherein the bottom portion is a separate component from the retaining ring, and wherein the retaining ring comprises a first hole and a second hole, each of the first hole and the second hole disposed within a bottom surface of the retaining ring, wherein, when the valve is assembled:

the second leg extends through the first hole; and the third leg extends through the second hole, and wherein at least one of the top portion and the bottom portion comprises a trough disposed therein, and wherein the trough comprises a center trough that fluidly connects the first leg to the fourth leg when the bottom portion is rotated about 90 degrees relative to the top portion, the center trough linearly extending through a center of the top portion or the bottom portion and comprising only a rectangular-shaped trough.

* * * * *